(12) United States Patent
Valenti et al.

(10) Patent No.: US 9,050,323 B2
(45) Date of Patent: Jun. 9, 2015

(54) METHODS OF TREATING DESTRUCTIVE INFLAMMATION OF THE MUCOUS MEMBRANES WITH LACTOFERRIN

(75) Inventors: Piera Valenti, Rome (IT); Rosalba Paesano, Isola del Liri (IT)

(73) Assignee: MICROBO S.R.L. (IT)

( * ) Notice: Subject to any disclaimer, the term of this patent is extended or adjusted under 35 U.S.C. 154(b) by 954 days.

(21) Appl. No.: 12/085,201

(22) PCT Filed: Apr. 5, 2006

(86) PCT No.: PCT/EP2006/003106
§ 371 (c)(1),
(2), (4) Date: May 19, 2008

(87) PCT Pub. No.: WO2007/065482
PCT Pub. Date: Jun. 14, 2007

(65) Prior Publication Data
US 2009/0156484 A1  Jun. 18, 2009

(30) Foreign Application Priority Data
Dec. 9, 2005 (IT) .............................. MI2005A2351

(51) Int. Cl.
A61K 38/40 (2006.01)
(52) U.S. Cl.
CPC ...................................... A61K 38/40 (2013.01)
(58) Field of Classification Search
CPC ..................................................... A61K 38/40
See application file for complete search history.

(56) References Cited

U.S. PATENT DOCUMENTS

| | | | |
|---|---|---|---|
| 5,198,419 A * | 3/1993 | Ando et al. ..................... 514/2.5 |
| 5,576,299 A | 11/1996 | Ando et al. |
| 5,834,424 A * | 11/1998 | Valenti et al. .................. 514/2.7 |
| 5,869,446 A * | 2/1999 | Valenti et al. .................. 514/2.5 |
| 6,333,311 B1 | 12/2001 | Nuijens et al. |
| 6,455,687 B1 | 9/2002 | Kruzel et al. |
| 7,026,295 B2 | 4/2006 | Varadhachary et al. ......... 514/12 |
| 7,323,442 B2 | 1/2008 | Yajima et al. ..................... 514/6 |
| 2002/0016289 A1 | 2/2002 | Conneely et al. |
| 2003/0229012 A1 | 12/2003 | Thomas |
| 2004/0152624 A1 | 8/2004 | Varadhachary et al. |

FOREIGN PATENT DOCUMENTS

| | | |
|---|---|---|
| EP | 0 559 425 A1 | 9/1993 |
| EP | 0 730 868 A | 9/1996 |
| EP | 0753308 A2 * | 1/1997 |
| EP | 1013283 A2 * | 2/2000 |
| EP | 1 068 871 A | 1/2001 |
| WO | WO 98/50076 A | 11/1998 |
| WO | WO 0172322 A2 * | 10/2001 |
| WO | WO 03099207 A2 * | 12/2003 |

OTHER PUBLICATIONS

Bezkorovaniny, (Adv Exp Med Biol. 1981;135:139-54, Abstract Only).*
Bullen et al., (Eur J Clin Microbiol Infect Dis. Aug. 1991;10(8):613-7, Abstract Only).*
Jurado (Clin Infect Dis. Oct. 1997.;25(4):888-95, Abstract Only).*
Pieracci et al., (Surg Infect (Larchmt). 2005;6 Suppl 1:S41-6, Abstract Only).*
Satue-Garcia et al., (J. Agric Food Chem. Oct. 2000; 48(10):4984-90; Abstract Only).*
ABC Health & Wellbeing Fact File on Herpes Simplex Virus (www.abc.net.au/health/library/stories/2005/05/05/1831287.htm)(first published May 5, 2005) (last accessed Nov. 6, 2014).*
Ajello et al., "Anti-invasive activity of bovine lactoferrin towards group A streptococci," Biochem. Cell Biol. 80(1):119-124, 2002.
Ammendolia et al., "Bovine lactoferrin inhibits echovirus endocytic pathway by interacting with viral structural polypeptides," Antiviral Res. 73(3):151-160, 2007.
Andrews, "Molecular control of iron metabolism," Best Pract. Res. Clin. Haematol. 18(2):159-169, 2005.
Arnold et al., "Antiadenovirus activity of milk proteins: lactoferrin prevents viral infection," Antiviral Res. 53(2):153-158, 2002.
Baker et al., "Molecular structure, binding properties and dynamics of lactoferrin," Cell. Mol. Life Sci. 62:2531-2539, 2005.
Belluzzi et al., "A new iron free treatment with oral fish cartilage polysaccharide for iron deficiency chronic anemia in inflammatory bowel diseases: A pilot study," World J. Gastroenterology 13(10):1575-1578, 2007.
Berlutti et al., "Both lactoferrin and iron influence aggregation and biofilm formation in Streptococcus mutans," BioMetals 17(3):271-278, 2004.
Berlutti et al., "Lactoferrin downregulates pro-inflammatory cytokines upexpressed in intestinal epithelial cells infected with invasive or noninvasive Escherichia coli strains," Biochem. Cell Biol. 84(3):351-357, 2006.
Berlutti et al., "Bovine lactoferrin inhibits the efficiency of invasion of respiratory A549 cells of different iron-regulated morphological forms of Pseudomonas aeruginosa and Burkholderia cenocepacia," Int. J. Immunopathol. Pharmacol. 21(1):51-59, 2008. (Abstract).
Bethell et al., "Recombinant human lactoferrin treatment for global health issues: iron deficiency and acute diarrhea," BioMetals 17(3):337-342, 2004.
Bezkorovainy, "Antimicrobial Properties of Iron Binding Proteins," Adv. Exp. Med. Biol. 135:139-154, 1981.

(Continued)

Primary Examiner — Cherie M Stanfield
(74) Attorney, Agent, or Firm — Cantor Colburn LLP

(57) ABSTRACT

Use of at least one transferrin, preferably lactoferrin, for preventing and/or treating destructive inflammation affecting mucous membranes, optionally associated with states of hypoferremia and/or anemia and/or acute and chronic infections. The destructive inflammation is caused, for example, by pathological conditions during pregnancy and by infections sustained by intracellular or adhered or biofilm-protected pathogens. The action of the transferrins described here is achieved by means of their topical and/or oral administration. A combined preparation for simultaneous, sequential or separate use is also described which comprises, as active components, a first composition for topical administration of at least one transferrin and a second composition for oral administration of at least one transferrin.

19 Claims, No Drawings

(56) References Cited

OTHER PUBLICATIONS

Bothwell, "Iron requirements in pregnancy and strategies to meet them," *Am. J. Clin. Nutr.* 72(Suppl):257S-264S, 2000.

Brock, "The physiology of lactoferrin," *Biochem. Cell Biol.* 80:1-6, 2002.

Bullen et al., "The Critical Role of Iron in Some Clinical Infections," *Eur. J. Clin. Microbiol. Infect. Dis.* 10(8):613-617, 1991.

Bullen et al., "Iron and Infection: the heart of the matter," *FEMS Immunol. Med. Microbiol.* 43:325-330, 2005.

Conneely, "Antiinflammatory Activities of Lactoferrin," *J. Am. Coll. Nutr.* 20(5):389S-395S 2001.

De Domenico et al., "The Molecular Mechanism of Hepcidin-mediated Ferroportin Down-Regulation," *Mol. Biol. Cell* 18:2569-2578, 2007.

Di Biase et al., "Heparin-Interacting Sites of Bovine Lactoferrin Are Involved in Anti-Adenovirus Activity," *J. Med. Virol.* 69(4):495-502, 2003.

Di Biase et al., "Effect of bovine lactoferrin on enteropathogenic *Yersinia* adhesion and invasion in HEp-2 cells," *J. Med. Microbiol.* 53(Pt. 5):407-412, 2004.

Fleming et al., "Orchestration of Iron Homeostasis," *N. Engl. J. Med.* 352(17):1741-1744, 2005.

Ganz, "Hepcidin—a regulator of intestinal iron adsorption and iron recycling by macrophages," *Best Pract. Res. Clin. Haematol.* 18(2):171-182, 2005.

Ganz, "Hepcidin and Its Role in Regulating Systemic Iron Metabolism," *Hematology Am. Soc. Hematol. Educ. Program*:29-35, 507, 2006.

Ganz et al., "Regulation of iron acquisition and iron distribution in mammals," *Biochim. Biophys. Acta* 1763:690-699, 2006.

Gasche et al., "Genotypes and Phenotypes in Crohn's Disease: Do They Help in Clinical Management?" *Gut* 54:162-67, 2005.

Giansanti et al., "Antiviral activity of ovotransferrin discloses an evolutionary strategy for the defensive activities of lactoferrin," *Biochem. Cell Biol.* 80(1):125-130, 2002.

Goldoni et al., "Metal complexes of lactoferrin and their effect on the intracellular multiplication of *Legionella pneumophila*," *BioMetals* 13(1):15-22, 2000.

Hernell et al., "Iron status of infants fed low-iron formula: no effect of added bovine lactoferrin or nucleotides," *Am. J. Clin. Nutr.* 76:858-864, 2002.

Hunter et al., "The Solution Structure of Human Hepcidin, a Peptide Hormone with Antimicrobial Activity That Is Involved in Iron Uptake and Hereditary Hemochromatosis," *J. Biol. Chem.* 277(40):37597-37603, 2002.

Jurado, "Iron, Infections, and Anemia of Inflammation," *Clin. Infect. Dis.* 25(4):888-895, 1997.

Longhi et al., "Influence of lactoferrin on the entry process of *Escherichia coli* HB101(pRI203) in HeLa cells," *Med. Microbiol. Immunol.* 182(1):25-35, 1993.

Longhi et al., "Effect of lactoferrin B, a pepsin-generated peptide of bovine lactoferrin, on *Escherichia coli* HB101(pRI203) entry into HeLa cells," *Med. Microbiol. Immunol.* 183(2):77-85, 1994.

Longhi et al., "Apoptotic death of *Listeria monocytogenes*-infected human macrophages induced by lactoferrin B, a bovine lactoferrin-derived peptide," *Int. J. Immunopathol. Pharmacol.* 18(2):317-325, 2005. (Abstract).

Longhi et al., "Lactoferrin inhibits early steps of human BK polyomavirus infection," *Antiviral Res.* 72(2):145-152, 2006.

Lönnerdal et al., "Absorption of iron from recombinant human lactoferrin in young US women," *Amer. J. Clinical Nutrition* 83(2):305-309, 2006.

Lönnerdal, "Nutritional roles of lactoferrin," *Curr. Opin. Clin. Nutr. Metab. Care* 12:293-297, 2009.

Loréal et al., "Hepcidin in Iron Metabolism," *Curr. Protein Pept. Sci.* 6:279-291, 2005.

Marchetti et al., "Lactoferrin inhibits herpes simplex virus type 1 adsorption to Vero cells," *Antiviral Res.* 29(2-3):221-231, 1996.

Marchetti et al., "Metal complexes of bovine lactoferrin inhibit in vitro replication of herpes simplex virus type 1 and 2," *BioMetals* 11(2):89-94, 1998.

Marchetti et al., "Inhibition of poliovirus type 1 infection by iron-, manganese- and zinc-saturated lactoferrin," *Med. Microbiol. Immunol.* 187(4):199-204, 1999.

Massucci et al., "Proteolytic activity of bovine lactoferrin," *BioMetals* 17(3):249-255, 2004.

Meier et al., "Prevention of Iron Deficiency Anemia in Adolescent and Adult Pregnancies," *Clin. Med. Res.* 1(1):29-36, 2003.

Nemeth et al., "Hepcidin Regulates Cellular Iron Efflux by Binding to Ferroportin and Inducing Its Internalization," *Science* 306:2090-2093, 2004.

Nemeth et al., "IL-6 mediates hypoferremia of inflammation by inducing the synthesis of the iron regulatory hormone hepcidin," *J. Clin. Invest.* 113(9):1271-1276, 2004.

Nemeth et al., "Regulation of Iron Metabolism by Hepcidin," *Annu. Rev. Nutr.* 26:323-342, 2006.

Nicolas et al., "Severe iron deficiency anemia in transgenic mice expressing liver hepcidin," *Proc. Natl. Acad. Sci. U.S.A.* 99(7):4596-4601, 2002.

Nicolas et al., "The gene encoding the iron regulatory peptide hepcidin is regulated by anemia, hypoxia, and inflammation," *J. Clin. Invest.* 110(7):1037-1044, 2002.

Paesano et al., "Oral administration of lactoferrin increases hemoglobin and total serum iron in pregnant women," *Biochem. Cell. Biol.* 84(3):377-380, 2006.

Paesano et al., "The influence of lactoferrin, orally administered, on systemic iron homeostasis in pregnant women suffering of iron deficiency and iron deficiency anaemia," *Biochimie* 91(1):44-51, 2009.

Pieracci et al., "Iron and the risk of infection," *Surg. Infect.* 6(Suppl. 1):S41-S46, 2005.

Pietrantoni et al., "Bovine Lactoferrin Inhibits Adenovirus Infection by Interacting with Viral Structure Polypeptides," *Antimicrob. Agents. Chemother.* 47(8):2688-2691, 2003.

Pietrantoni et al., "Bovine lactoferrin peptidic fragments involved in inhibition of Echovirus 6 in vitro infection," *Antiviral Res.* 69(2):98-106, 2006.

Puddu et al., "Antiviral effect of bovine lactoferrin saturated with metal ions on early steps of human immunodeficiency virus type 1 infection," *Int. J. Biochem. Cell Biol.* 30(9):1055-1062, 1998.

Puddu et al., "Role of endogenous interferon and LPS in the immunomodulatory effects of bovine lactoferrin in murine peritoneal macrophages," *J. Leukoc. Biol.* 82(2):347-353, 2007.

Puddu et al , "Immunomodulatory effects of lactoferrin on antigen presenting cells," *Biochimie* 91(1):11-18, 2009.

Rossi et al., "$Ca^{2+}$ binding to bovine lactoferrin enhances protein stability and influences the release of bacterial lipopolysaccharide," *Biochem. Cell Biol.* 80(1):41-48, 2002.

Santapaola et al., "Effect on bovine lactoferrin on the activation of the enteroinvasive bacterial type III secretion system," *BioMetals* 17(3):261-265, 2004.

Scholl, "Iron status during pregnancy: setting the stage for mother and infant," *Am. J. Clin. Nutr.* 81(Suppl.):1218S-1222S, 2005.

Seganti et al., "Involvement of bovine lactoferrin moieties in the inhibition of herpes simplex virus type 1 infection," *Int. J. Immunopathol. Pharmacol.* 14(2):71-79, 2001. (Abstract).

Siciliano et al., "Bovine Lactoferrin Peptidic Fragments Involved in Inhibition of Herpes Simplex Virus Type 1 Infection," *Biochem. Biophys. Res. Commun.* 264(1):19-23, 1999.

Superti et al., "Antirotaviral activity of milk proteins: lactoferrin prevents rotavirus infection in the enterocyte-like cell line HT-29," *Med. Microbiol. Immunol.* 186(2-3):83-91, 1997.

Superti et al., "Involvement of bovine lactoferrin metal saturation, sialic acid and protein fragments in the inhibition of rotavirus infection," *Biochem. Biophys. Acta.* 1528(2-3):107-115, 2001.

Superti et al., "Inv-mediated apoptosis of epithelial cells infected with enteropathogenic *Yersinia*: A protective effort of lactoferrin," *Res. Microbiol.* 156(5-6):728-737, 2005.

Tinari et al , "Inhibitory activity of bovine lactoferrin against echovirus induced programmed cell death in vitro," *Int. J. Antimicrob. Agents* 25(5):433-438, 2005.

(56) References Cited

OTHER PUBLICATIONS

Tsuji et al., "Human Intelectin Is a Novel Soluble Lectin That Recognizes Galactofuranose in Carbohydrate Chains of Bacterial Cell Wall," *J. Biol. Chem. 276*(26):23456-23463, 2001.
Valenti et al., "Antiviral Activity of Lactoferrin," *Adv. Exp. Med. Biol. 443*:199-203, 1998.
Valenti et al., "Apoptosis of Caco-2 Intestinal Cells Invaded by *Listeria monocytogenes*: Protective Effect of Lactoferrin," *Exp. Cell. Res. 250*(1):197-202, 1999.
Valenti et al., "Lactoferrin Functions: Current Status and Perspectives," *J. Clin. Gastroenterol. 38*(Suppl. 2):S127-S129, 2004.
Valenti et al., "Lactoferrin: an important host defence against microbial and viral attack," *Cell Mol. Life Sci. 62*(22):2576-2587, 2005.
Visca et al., "Interaction of lactoferrin with *Escherichia coli* cells and correlation with antibacterial activity," *Med. Microbiol. Immunol. 179*(6):323-333, 1990.
Von Hunolstein et al., "Lack of activity of transferrins towards *Streptococcus* spp.," *Med. Microbiol. Immunol. 181*(6):351-357, 1992.
Ward et al., "Lactoferrin and host defense," *Biochem. Cell. Biol. 80*(1):95-102, 2002.
Ward et al., "Iron Status in Mice Carrying a Targeted Disruption of Lactoferrin," *Molecular and Cellular Biology 23*(1):178-185, 2003.
Ward et al., "Lactoferrin: Role in iron homeostasis and host defense against microbial infection," *BioMetals 17*(3):203-208, 2004.
Ward et al., "Multifunctional roles of lactoferrin: a critical overview," *Cell Mol. Life Sci. 62*(22):2540-2548, 2005.
Weinstein et al., "Inappropriate expression of hepcidin is associated with iron refractory anemia: implications for the anemia of chronic disease," *Blood 100*(10):3776-3781, 2002.
Davidson et al., "Specific binding of lactoferrin to brush-border membrane: ontogeny and effect of glycan chain," *Am. J. Physiol. 254* (Gastrointest. Liver Physiol. 17):G580-G585, 1988.
Lönnerdal et al., "Lactoferrin: Molecular Structure and Biological Function," *Annu. Rev. Nutr. 15*:93-110, 1995.
Shin et al., "Recombinant Human Intelectin Binds Bovine Lactoferrin and Its Peptides," *Biol. Pharm. Bull. 31*:1605-1608, 2008.
Suzuki et al., "Molecular Cloning and Functional Expression of a Human Intestinal Lactoferrin Receptor," *Biochemistry 40*:15771-15779, 2001.
Wessling-Resnick, "Iron Homeostasis and the Inflammatory Response," *Annu. Rev. Nutr. 30*:105-122, 2010.

\* cited by examiner

METHODS OF TREATING DESTRUCTIVE INFLAMMATION OF THE MUCOUS MEMBRANES WITH LACTOFERRIN

CROSS-REFERENCE TO RELATED APPLICATIONS

This application is a U.S. national stage application filed under 35 U.S.C. §371 of International Patent Application PCT/EP2006/003106, accorded an international filing date of Apr. 5, 2006, which claims the benefit of Italian Patent Application No. MI2005A002351 filed Dec. 9, 2005, all of which are incorporated herein by reference in their entirety.

TECHNICAL FIELD

The present invention relates to a new pharmaceutical use of transferrins and to a combined preparation for simultaneous, sequential or separate use, which comprises transferring.

BACKGROUND ART

Human mucous membranes, generally colonized by commensal bacteria, are the habitat that is most exposed to the aggression of pathogenic microorganisms and viruses. In physiological situations, mucosal secretions, constituted by several proteins and peptides of natural immunity, ensure protection against microbial and viral attack. Inflammatory response is a fundamental defense mechanism against infections which is implemented by the host, but in some conditions it can become so intense as to be harmful. In such cases, the immunotolerance of the host with respect to commensal microorganisms becomes an adaptive immune response against pathogens, which creates an inflammation which is termed "destructive" because it is always accompanied by significant damage to the cells of the host. Therefore, the balance between physiological inflammation and destructive inflammation, together with the regulatory mechanisms that limit inflammatory response and restore, when necessary, homeostasis of the inflammation (physiological inflammation), are essential, because they ensure inhibition of destructive phenomena which might, for example, combine with damage caused by infectious disorders already in progress, and the mucous membranes themselves, damaged and lacking the non-antibody factors of natural immunity, might become more susceptible to the onset of any infection. The onset of a pathological and destructive inflammation can be caused by the persistence of a stimulus that the body recognizes as foreign and tends to eliminate unsuccessfully. Typical cases are, for example, destructive inflammations following more or less pathological pregnancies, and especially following viral infections, mycoses or infections caused by bacteria (both Gram-positive and Gram-negative) which are localized intracellularly or which, once they have adhered to the cells of the body, synthesize, and cover themselves, with a more or less thick layer of polysaccharides, which together with the microorganisms constitutes the so-called biofilm, which is known to be impermeable to ordinary bactericidal and bacteriostatic agents.

One common and important incidental disorder of destructive inflammation is constituted by more or less severe states of hypoferremia and/or anemia. During inflammation there is in fact a gradual transfer of free iron from circulation to the tissues, increasing considerably the physiological concentration of free iron at the mucus membrane level (approximately $10^{-18}$ M). This fact has several harmful consequences for the body, including (i) an overproduction, at tissue level, of reactive oxygen species, above all superoxides (by means of the iron-induced Fenton reaction), and (ii) an increase in the production of proinflammatory cytokines. Moreover, it has been demonstrated that an increase in the iron that is available or free at the level of the mucous membranes facilitates microbial and viral proliferation and dissemination, since many pathogens exhibit both growth and virulence induced by iron. Finally, the presence of infections of the mucous membranes of the oral cavity (for example parodontopathies), of the intestine (enteritides) or of the vaginal epithelium in progress, in turn leads to bleeding and to a further withdrawal of iron from circulation; these factors increase the overload of iron in the tissues (to the point of creating states of chronic anemia caused by infections and consequent inflammations), in a sort of positive feedback. All of the above explains why the onset of a destructive phlogosis at the level of the mucous membranes is often associated with pathological conditions of hypoferremia and/or anemia and/or infections affecting said mucous membranes, to the point in which the roles of cause and consequence among the various disorders are hard to distinguish.

Currently, states of chronic inflammation possibly associated with hypoferremia, anemia and acute or chronic infections are treated by administering substances that are specific for each symptom, such as antibiotics, antivirals, antiinflammatories or iron-based therapies, thus requiring the combination of drug cocktails if two or more of these complications are present simultaneously. However, there are no drugs capable of having an appreciable therapeutic effect on more than one component simultaneously.

The aim of the present invention is, therefore, to provide for the use of a substance for preparing a medicament for preventing and/or treating destructive inflammation affecting mucous membranes, optionally associated with states of hypoferremia and/or anemia and/or acute or chronic infections.

Within the scope of this aim, an object is to provide a composition for treating and preventing the therapeutic indications mentioned above which allows to achieve a particularly effective and potent effect.

DISCLOSURE OF THE INVENTION

This aim and other objects are achieved by the use of at least one transferrin, preferably lactoferrin, to prepare a medicament for preventing and/or treating, topically and/or orally, destructive inflammation affecting the mucous membranes, optionally associated with states of hypoferremia and/or anemia and/or acute or chronic infections.

The aim and objects of the invention are also achieved by a combined preparation for simultaneous, sequential or separate use, particularly for preventing and/or treating very effectively destructive inflammation affecting mucous membranes, optionally associated with states of hypoferremia and/or anemia and/or acute or chronic infections, wherein said preparation comprises, as active components, a first pharmaceutical composition for topical use of at least one transferrin, preferably lactoferrin, and a second pharmaceutical composition for oral use of at least one transferrin, preferably lactoferrin.

It is understood that any characteristic that is mentioned with reference to just one of the aspects of the invention but can also be referred to other aspects must be considered equally valid with reference to these latter aspects even though it is not repeated explicitly.

Ways of Carrying Out the Invention

The various aspects of the present invention derive from surprising observations made by the Applicant, according to which topical and/or oral administration of transferrins is capable of achieving simultaneously a series of effects, including:

i) a bacteriostatic/fungistatic and bactericidal/fungicidal action, since transferrins, especially lactoferrin, sequester iron, preventing microbial growth and dissemination and at the same time have an action against viruses, preventing early virus-host cell interactions;

ii) restoration of the homeostasis of the inflammation, since transferring, especially lactoferrin, on the one hand reduce the expression and synthesis of proinflammatory cytokines, above all interleukin-1β, interleukin-6, interleukin-8, TNF-α and NF-kB, the overproduction whereof is a characteristic and distinctive sign of destructive inflammation. There is, therefore, a consequent protection against cell damage and an augmentation of the natural defenses of the host, on the other hand, they sequester free iron, blocking the overproduction of active species of oxygen, which are also involved in the activation of proinflammatory cytokines;

iii) restoration of iron homeostasis, since transferring, especially lactoferrin, by inhibiting the expression and synthesis of IL-6 and consequently of hepcidin, allow ferroportin to return into circulation the iron that has accumulated in the tissues. The positive action performed on the release of iron from tissues also has as an important consequence the reduction (prevention factor) of the susceptibility of said tissues to being attacked by microbial, mycotic and viral infections, iv) a positive action on restoration of the physiological values of sideremia and hemoglobin, solving, thanks to the already-mentioned effect on the transfer of iron from tissues to circulation, states of hypoferremia and/or anemia associated with microbial and viral infections and with inflammatory phenomena which are a consequence or not of infections.

Lactoferrin, like transferrins in general, has long been known for its antibacterial activity and for its bactericidal activity. Recently, its ability to inhibit the microbial adhesion and penetration of pathogenic bacteria known as facultative intracellular bacteria has also been highlighted. Moreover, the capacity of lactoferrin to inhibit the early stages of a viral infection has been demonstrated extensively. However, it had never been demonstrated or suggested that transferrins and especially lactoferrin could be used to block phenomena of destructive phlogosis (inhibiting the production of superoxides and proinflammatory cytokines), simultaneously eliminating the overload of iron in the mucous membranes, which is a cause of microbial proliferation and dissemination and of states of anemia and hypoferremia often associated with the destructive inflammation itself. Although one does not wish to be bound by any specific scientific theory, it is believed that the coordinated actions performed by transferrins when used according to the invention may be attributable to the dual action of sequestration of free iron and inhibition of the synthesis of proinflammatory cytokines, especially IL-6, without excluding the characteristic capacity of lactoferrin (a highly cationic glycoprotein) to bind to any component having a negative charge which is present on the surfaces of microorganisms, viruses and host cells. The first effect leads to a reduction of the formation of reactive oxygen species, which contribute to the onset of a destructive inflammation, while the second effect entails a parallel reduction of the synthesis of hepcidin by means of a parallel reduction of interleukin-6 and of other proinflammatory cytokines. Hepcidin has an inhibitory role on the activity of ferroportin, which is a protein whose task is to carry iron from the inside to the outside of cells. Therefore, when hepcidin is absent or scarcely expressed because interleukin-6 returns to normal expression and normal synthesis levels, ferroportin is free from the bond with hepcidin and can transport the iron from the tissues to circulation. By restoring first of all a physiological immune response and eliminating the iron needed for microbial growth and dissemination, the invention is a valid aid in preventing and treating also infections which are currently difficult to eradicate, such as those caused by pathogens (bacteria, viruses or fungi) which are protected by biofilm or are localized in intracellular areas which are scarcely or not at all accessible to drugs.

The expression "destructive (or pathological) inflammation (or phlogosis)" is used to designate an inflammation in response to pathogens characterized by overproduction of interleukin-1β, interleukin-6, interleukin-8, TNF-α and NF-kB, which inflammation causes damage to the cells of the host. Verification of the onset of this condition and its distinction with respect to a nondestructive inflammation are aspects which fall within the knowledge of a person skilled in the art.

The expression "hypoferremia and/or anemia associated with destructive inflammation" means preferably that the states of hypoferremia and anemia, individually or as a whole, are caused by in destructive inflammation affecting the mucous membranes. The expression "acute and chronic infective disorders or infections associated with destructive inflammation" means preferably that these infections cause destructive inflammation. The expression "cause destructive inflammation" means preferably that infections caused by pathogens or commensal bacteria that have become occasional pathogens are a factor of increased risk for the onset of destructive phlogosis and can persist and relapse or become chronic also as a consequence of the onset of destructive inflammation. Thanks to the peculiar and advantageous properties of transferrins and in particular of lactoferrin, it is particularly advantageous to use the invention to prevent and/or treat destructive inflammation, hypoferremia, anemia and acute or chronic infections in situations in which all these components are present simultaneously.

The expression "prevent and/or treat destructive inflammation" means reducing the severity or frequency of the symptoms of this condition, of its causes or of its consequences. In particular, it means reducing and maintaining at physiological values the production of interleukin-1β, interleukin-6, interleukin-8, TNF-α and NF-kB and hepcidin. It should be noted that there is no intention to describe or claim an immunosuppressive effect, but only an effect of control of the homeostasis of the inflammatory process with respect to destructive inflammation and not against a normal physiological inflammation, where the expression "normal physiological inflammation" designates an inflammatory process which does not entail overproduction of the proinflammatory cytokines mentioned above.

The expression "prevent and/or treat hypoferremia and anemia" means to restore physiological levels of sideremia and amount of hemoglobin in circulation.

The expression "acute or chronic infections" designates infectious disorders affecting the mucous membranes and caused by intracellular pathogens (bacteria or viruses), microorganisms which have adhered or are protected in a biofilm. No reference is made instead to the type of pathogen (bacterium, virus, fungi or protozoa). Preferably, infections are one or more among gingivitides, parodontopathies, mycotic infections and viral infections in general, relapsing infections caused by microorganisms known to be in biofilm form and microorganisms known to have a facultative or obligatory intracellular localization, as in the case of viruses.

The expressions "restoration of iron homeostasis" or "restoration of iron metabolism" means restoring a physiological distribution of the amount of iron between tissues and circulation, as well as restoring the physiological operation of the natural systems meant to maintain this distribution.

The expression "mucous membranes" preferably designates one or more among intestinal, vaginal, anal mucous membranes, and mucous membranes of the oropharyngeal cavity. If use is topical, the mucous membranes are one or more among vaginal mucous membranes, anal mucous membranes and mucous membranes of the oropharyngeal cavity.

The expressions "topical administration" or "topically" or "medicament for topical administration" designate a local administration of transferrins, preferably an administration in one or more among the oropharyngeal cavity, the vaginal cavity, and the anal cavity. Although it is technically possible at present to achieve topical administration also by oral administration (in which, therefore, the transferrins are not absorbed but act only locally on the intestinal mucous membrane), in the present invention an enteral pharmaceutical form should not be understood as "for topical administration". Therefore, the prevention and/or treatment of intestinal mucous membranes occurs always and only by means of an oral administration which combines topical effect and systemic effect.

The expressions "oral administration", "orally" or "medicament for oral administration" designate systemic and topical oral administration, which therefore allows both systemic absorption of transferrins and their local activity. Transferrins administered by means of an oral medicament therefore entail both a local topical effect on the intestinal mucous membranes and a systemic effect on all the mucous membranes of the body after their gastrointestinal absorption.

As described in detail hereinafter, regardless of the involved mucous membrane, in case of destructive inflammation associated with hypoferremia and/or anemia, the use of transferrins and particularly of lactoferrin preferably occurs according to a dual topical and oral mode. Of course, treatment of the intestinal mucous membranes does not require a dual administration mode.

The term "transferrins" designates a class of glycoproteins which are present in nature and are characterized by the presence of two bonding sites for iron (III) and by a high homology of sequence among the various members of the class. Molecules which belong to the class of transferrins and can be used in the invention are lactoferrin, serotransferrin and ovotransferrin, highly preferably lactoferrin. It is possible to use the individual molecules as such or mixed together.

It has been found surprisingly that the effect on phlogosis obtained with transferrins can be achieved for any degree of saturation of the bonding sites for iron (III), be they completely free ("apo" form of lactoferrin, degree of saturation of iron sites equal to 0%), partially already occupied or completely already saturated ("holo" form of lactoferrin, degree of saturation of iron sites equal to 100%). In any case, it should be noted that there is a dependency between exhibited activity and saturation percentage (but not between activity and total quantity of contained iron), in that the higher the presence of transferrin at a lower degree of saturation, the higher the achievable activity. However, a completely saturated transferrin (100% degree of saturation) does not exhibit an appreciable therapeutic effect on inhibition of superoxides, which as mentioned are one of the causes of destructive inflammation. The reduced capacity of 100% iron-saturated transferrins to inhibit the expression and synthesis of proinflammatory cytokines is due to this missing function. It is also understood that the transferrins usable in the invention may have any degree of saturation of the iron bonding sites ranging from 0% saturation to 100% saturation, preferably from 0% (including this limit) to 100% (excluding this limit), more preferably from 0% to 20% (including these limits) of saturation. It is possible to use a transferrin having a specific degree of saturation or a mixture of transferrins with different degrees of saturation. It is particularly preferred to use transferrins having a low degree of saturation. It is also understood that the bonding sites for iron can be occupied at any degree of saturation by Fe (III) and/or optionally, with different kinetics and affinities, by one or more other transition metals which have similar chemical and physical properties. These metals can be for example one or more among Zn, Cu, Mn.

The term "lactoferrin" designates both the intact native protein and the intact recombinant protein, as well as fragments of the intact (native or recombinant) protein, which can be obtained by means of its enzymatic or chemical digestion. Lactoferrin, highly preserved in the various species, is a glycoprotein constituted by 692 amino acids in the human form, with an isoelectric point of approximately 9, a molecular weight of approximately 80 kDa, with three potential glycosylation sites. It can bind reversibly two atoms of Fe(III) per molecule with high affinity ($K_D \sim 10^{-20}$ M) (this ability to bind iron is also maintained by the lobes and by the various fragments described above). Lactofernin is present, for example, in milk and in all human secretions and in neutrophil granules. The advantage of using lactoferrin instead of the other transferrins arises from the ability of lactoferrin to bind iron with greater affinity and to bind it even at acid pH values, which occur at infection sites. Lactoferrin can be produced in large quantities by extraction from cow's milk. In the tests that will be described in the present patent, bovine lactoferrin was used, but all other currently commercially available lactoferrins, such as for example human lactoferrin, murine lactoferrin and buffalo lactoferrin, have the same activity. It is understood that lactoferrin can be natural (obtained by extraction), produced by recombinant methods, or a mixture of the two types. All the preparations of transferring, preferably lactoferrin, despite having a different degree of saturation, except for the form completely saturated with iron, have exhibited the same effectiveness in inhibiting the expression and synthesis of inflammatory cytokines and restoration of iron homeostasis; moreover, the 100% saturated preparation has low activity in removing iron from tissues.

It has also been found surprisingly that the same properties exhibited by intact transferrins can also be achieved by using individual parts thereof, which can be obtained by enzymatic digestion of the whole protein. For this reason, it is understood that the use of transferrins as defined above can be replaced with the use of one or more of their fragments which can be obtained by enzymatic digestion and purification. In the case of lactoferrin, preferred fragments are lobe N and lobe C and parts of said lobes, for example fragments aa 86-258 MW 20 KDa and aa 285-692 MW 47 KDa. The expression "lobe N" designates the fraction having a molecular weight (MW) of approximately 33 KDa, which corresponds to the fragment from 1 to 280 and part of said lobe with a molecular weight of approximately 20 KDa, which corresponds to the fragment from amino acid 86 to 258 of the intact lactoferrin digested enzymatically and then purified. The expression "lobe C" designates the fraction having a molecular weight of approximately 38 KDa, which corresponds to the fragment 345-692, and another fraction having a molecular weight of 47 KDa, which corresponds to the fragment from 285 to 692 of the intact lactoferrin digested enzymatically and subsequently purified.

The expression "composition or medicament comprising transferring" designates a composition or medicament which has transferrins, preferably lactoferrin, as defined above, as its only, main (in terms of percentage by weight or volume) or minority (in terms of percentage by weight or volume) active ingredient. Transferrins, and lactoferrin in particular, can be used in any known liquid, semisolid or solid pharmaceutical form, for topical and oral administration, optionally in combination with excipients or pharmaceutically acceptable carriers. It is also understood that if requested, the transferrins and lactoferrin in particular can be used also in association with one or more conventional drugs having an anti-inflammatory, antibacterial (both bacteriostatic and bactericidal), antiviral, antimycotic, iron-based activity. It has been found surprisingly that topical administration of transferrins has achieved higher activity on the components of destructive inflammation and acute or chronic infection, while it has been found to be less active in resolving states of hypoferremia and anemia associated with destructive inflammation. Oral administration of transferrins has instead exhibited marked activity also on restoration of iron homeostasis (therefore in resolving states of hypoferremia and anemia). For this reason, topical use of transferrins according to the invention is advantageously combined with oral use thereof if, for example, the maximum effect is to be obtained also on states of hypoferremia and anemia associated with destructive inflammation. Preferred pharmaceutical forms for topical administration are selected among freeze-dried anhydrous powders for direct use (for example, freeze-dried powders for sprinkling), ready for use or extemporaneous water-based solutions (for example, solutions for rinses or washes), gels, creams, tablets to be dissolved in the mouth, vaginal tablets, toothpastes, chewing gums, freeze-dried products to be frozen. The pharmaceutical form of freeze-dried product to be distributed directly on the oral or vaginal mucous membranes is the form that has demonstrated the highest effectiveness. In order of decreasing preference it is followed by tablets, creams or gels, and extemporaneous solutions. As regards the pharmaceutical forms for oral administration, every currently known pharmaceutical form that can be ingested has been found to be effective. However, the best results in terms of resolving intestinal infections and in treating and preventing hypoferremia and anemia have been obtained with capsules or tablets containing lactoferrin and, to a slightly lesser extent, with lactoferrin dissolved at the time of use in an aqueous solution.

In a second aspect, the invention relates to a combined preparation for simultaneous, sequential or separate administration, which comprises, as its active components, a first pharmaceutical composition for topical administration, which comprises at least one transferrin, preferably lactoferrin, and a second pharmaceutical composition for oral administration, which comprises at least one transferrin, preferably lactoferrin. Among the advantages achieved by the preparation according to the invention there is the advantage of simultaneously solving states of destructive inflammation that occur together with hypoferremia and anemia. Currently known products and compositions (including normal compositions of transferrin not formulated as a combined preparation for topical and oral use) are unable to achieve such an effect simultaneously.

The two compositions of the preparation can be defined by means of same required and optional characteristics indicated regarding the pharmaceutical forms for topical and/or oral administration described above in the context of the use of transferrins.

The two compositions are now described by way of example with reference only to lactoferrin. The person skilled in the art, by referring to his ordinary knowledge, will know in any case how to adapt immediately this information to other transferrins as well.

In order to obtain an appreciable effect on all the components of acute or chronic infection, destructive inflammation, hypoferremia and anemia, it is highly advantageous to follow the dosage regimen described below.

If the first (topical) composition is in a single-dose solid form (for example, vaginal lozenges, pastilles and tablets), preferably the total quantity of lactoferrin administered ranges from 100 mg to 400 mg of lactoferrin per day, advantageously for one week. The same interval is also preferred in the case of solid multiple-dose pharmaceutical compositions (for example, freeze-dried powder to be collected in each instance). One can choose whether to administer lactoferrin once a day or spread it over multiple applications per day. Preferred examples of first composition for topical administration are lozenges, pastilles and tablets which comprise 50 mg to 200 mg of lactoferrin to be administered twice a day for one week, vaginal tablets which comprise 50 mg to 200 mg of lactoferrin to be dissolved twice a day for one week, freeze-dried lactoferrin to be dispersed in situ twice a day in an amount equal to 50-200 mg per application, for one week, freeze-dried lactoferrin to be frozen and to be used to massage the gums several times per day in an amount equal to 10-30 mg per application.

If the first composition is in liquid or semisolid multiple-dose form (for example, a solution for rinses, gels, creams), the amount of lactoferrin contained therein is comprised advantageously in the range 0.1-10% weight/volume of composition. It is advantageous to stay, in this case also, within the range of 100-400 mg of lactoferrin per day, advantageously for one week, indicated above for solid compositions.

If the second (oral) composition is in solid and single-dose form (for example tablets), preferably the total amount of lactoferrin that is administered ranges from 50 mg to 200 mg per day, advantageously for one month, more preferably equal to 200 mg per day, advantageously for one month. For example, it is possible to administer twice a day freeze-dried anhydrous powder containing 100 mg of lactoferrin each, for one month.

It is also advantageous for the administrations of the first and second compositions as defined above to occur away from meals.

The dosage quantities and timings indicated above (defined as a whole "dosage regimens"), including the specific examples of topical and oral compositions, are to be considered valid and preferred aspects also in relation to the pharmaceutical use of transferrins and to the corresponding medicaments described above.

By way of example, the effectiveness in vitro of lactoferrin in prevention and treatment of gingivitides, viral gingivostomatitides, and parodontopathies is now described by using cultures of gingival fibroblasts affected by supragingival plaque bacteria, by type 1 Herpesvirus and Gram-negative anaerobic bacteria of subgingival plaque, associated with parodontopathies. The addition of lactoferrin reduces the high expression and synthesis of proinflammatory cytokines produced by infected epithelial cells and inhibits the production of superoxides, which in particular activate NF-kB, which in turn induces the cascade of proinflammatory cytokines. Lack of activation of NF-kB thus prevents cell damage and consequent dissemination of microbial and viral infections. In in vivo tests, the effectiveness of lactoferrin administered topically and orally in the case of hypoferremia and anemia, in preventing and treating gingivitides, viral gingivostomatitides and parodontopathies is assessed not only by local objective examination but also by clinical parameters, such as the concentration of proinflammatory cytokines and hepcidin in the blood or of the latter also in urine, and by hematological parameters, with particular attention to the values of sideremia and hemoglobin before and after treatment. In vivo, the reduced inflammation due to lactoferrin allows the lactoferrin also to be able, by means of proteins which modulate the inflow and outflow of iron in and from the cells (ferroportin), to remove iron from the tissues and transfer it to the circulation, preventing in tissues formation of superoxides and at the same time inhibiting microbial replication and restoring in circulation the values of sideremia and hemoglobin. Moreover, again by way of example, the effectiveness of lactoferrin in treating mycotic infections by *Candida albicans* is illustrated, by using in vitro cultures of fibroblasts as a model of oral mycoses and by using in vitro cultures of HeLa cells (derived from uterine carcinoma), also infected by *Candida albicans*, as a model of vaginal mycoses. In both kinds of infection, the addition of lactoferrin powerfully inhibits expression and synthesis of interleukin-6 by the cultured cells. In vivo, the reduced inflammation allows the lactoferrin, by means of proteins which modulate the inflow and outflow of iron in and from the cells, to be also able to remove iron from tissues, preventing formation of superoxides and at the same time inhibiting microbial replication. In these mycotic infections also, in case of severe hypoferremia and anemia, topical administration combined with oral administration in the prevention and treatment of infections of gingival or vaginal mucous membranes by mycetes is assessed not only by local objective examination but also by clinical parameters, such as the concentration of proinflammatory cytokines and hepcidin in the blood or of the latter also in urine, and by hematological parameters, with particular attention for the values of sideremia and hemoglobin before and after the treatment.

Moreover, again by way of example, the effectiveness of lactoferrin in treating intestinal infections is illustrated by using facultative intracellular bacteria such as *Salmonella* spp., which infect in vitro cultures of intestinal cells as a model of microbial enteritides. The presence of lactoferrin in infected cell cultures powerfully inhibits expression and synthesis of proinflammatory cytokines produced by infected epithelial cells and of reactive oxygen species. The reduced inflammation allows the lactoferrin, by means of proteins which modulate the inflow and outflow of iron in and from the cells, to be also able, to remove iron from the tissues, preventing formation of superoxides, which also activate NF-kB. Lack of activation of NF-kB, which in turn induces the cascade of proinflammatory cytokines, on the part of lactoferrin, which prevents formation of superoxides, in fact prevents cell damage and the consequent microbial replication and dissemination of the infection.

In in vivo tests, the effectiveness of lactoferrin administered orally in preventing and treating enteritides is assessed not only by objective examination but also by means of clinical parameters, such as the concentration of proinflammatory cytokines and of hepcidin in blood or of the latter also in urine, and by hematological parameters, with particular attention to the values of sideremia and of hemoglobin before and after treatment.

The use of lactoferrin and of transferrins more generally in the prevention and therapy of infectious and inflammatory pathologies of human mucous membranes, including intestinal, vaginal and oral cavity mucous membranes, with particular reference to gingivitides, mycotic and viral infections, and parodontopathies, and the ability to increase sideremia and hemoglobin, are only some of the possible therapeutic applications of the activity of simultaneously inhibiting expression and synthesis of proinflammatory cytokines, superoxide production and, by means of the transport of iron from tissues to circulation, of restoring normal values of sideremia and hemoglobin described in the present patent. These properties of lactoferrin in fact allow its use to prevent and treat many other acute and relapsing inflammations and infections affecting mucous membranes.

The examples given here show that the preventive and therapeutic activity with respect to infectious and inflammatory disorders of mucous membranes possessed by lactoferrin and by transferrins in general can be used against infectious and inflammatory disorders affecting human mucous membranes, including intestinal, vaginal and oral cavity mucous membranes, with particular reference to disorders selected among gingivitides, mycotic and viral infections, parodontopathies, hypoferremia, anemia, and other acute and relapsing disorders, and can be considered extremely advantageous with respect to the treatments currently in use, for example because it is characterized by lack of toxicity and because it is the only substance capable of performing simultaneously multiple combined functions, which comprise especially homeostasis of iron and of destructive inflammation. In particular, lactoferrin, by inhibiting the synthesis of interleukin-6, consequently prevents the synthesis of hepcidin, modulated by interleukin-6, restoring the action of ferroportin, which is otherwise inhibited by hepcidin, the activity whereof allows the transport of iron from tissues to circulation, restoring physiological values of sideremia and hemoglobin, which is fundamental both for the health of the host and for the prevention and therapy of mucous membrane disorders. Moreover, in the case of the treatment of parodontopathies, lactoferrin replaces, with a higher therapeutic success rate, an expensive and invasive technique such as the surgical removal of subgingival plaque, which solves the problem only for brief periods, after which repeated infectious and inflammatory relapses appear until complete loss of the tooth attachment and partial loss of the bone occur.

Other characteristics and advantages of the present invention will become better apparent from the description of the following preferred embodiments, understood merely by way of non-limiting example.

EXAMPLE 1

Activity of lactoferrin in gingivitides. The experimental regimen used consists of:

Microorganisms: the microorganisms were obtained by inoculating directly a plaque taken from a patient affected by gingivitis and used at a microbial concentration of the various microbial genera of $10^7$ microorganisms/ml.

Cell monolayer: gingival fibroblasts were cultured until a semiconfluent monolayer of $10^5$ cells/ml was obtained.

Infection of the cell monolayer: the monolayer of gingival fibroblasts was inoculated with $10^7$ bacteria/ml of plaque in order to have an infection microbial multiplicity of 100:1 in the absence or presence of 60 µg/ml of bovine lactoferrin saturated in iron at 15-30% and incubated for 2 hours at 37° C.

Dosage of cytokine expression: the supernatant of the monolayer was collected and centrifuged in order to remove the bacteria. After repeated centrifuging, the supernatant without bacteria was frozen at −20° C. for analysis of the production of any cytokines induced by the infection. The monolayer was instead repeatedly washed with PBS without $Ca^{2+}$ and $Mg^{2+}$ in order to remove both bacteria and any traces of lactoferrin, in the conditions in which it was added, and lysed in order to extract the RNAs from the fibroblasts and test them for gene expression in comparison with those extracted from non-infected cells or cells infected in the absence of lactoferrin, by means of a Microarray.

Dosage of the production of expressed cytokines: the preserved supernatant was used to dose the produced cytokines by means of an immune enzymatic test (ELISA), specific for each one of the cytokines to be tested.

Superoxide Assay

The production of the reactive oxygen species is measured by adding ferricytochrome c to the epithelial cells in culture. The assay was based on the reduction of ferricytochrome c.

The results of the experiments are summarized below:

Among the 300 genes that were analyzed, the infection of the monolayer induced a higher gene expression with respect to non-infected cells by approximately 1 or 2 times only for interleukin 6, interleukin 8 and TNF-α. The addition of lactoferrin reduced the expression of these cytokines, returning them to a normal expression value. Quantitative analysis of the synthesis of interleukin 6, of interleukin 8 and of TNF-α confirmed the data related to gene expression of said proinflammatory cytokines, as shown in Table 1.

TABLE 1

Expression and synthesis of interleukin 6 (IL-6), interleukin 8 (IL-8) and TNF-α in gingival fibroblasts which are infected or not with supragingival plaque in the absence or presence of lactoferrin (60 μg/ml).

|  | Without lactoferrin | | | With lactoferrin | | |
| --- | --- | --- | --- | --- | --- | --- |
|  | IL-6 | IL-8 | TNF-α | IL-6 | IL-8 | TNF-α |
| Expression in non-infected cells | 1.0 | 1.0 | 1.0 | 1.0 | 1.0 | 1.0 |
| Expression in infected cells | 1.5 | 2.0 | 2.0 | 1.0 | 1.0 | 1.0 |
| Synthesis in non-infected cells (pg/ml) | 90 | 2.100 | 22 | 90 | 2.100 | 22 |
| Synthesis in infected cells (pg/ml) | 190 | 4.100 | 40 | 105 | 1.900 | 29 |

The value 1.0 listed in the Table refers to normal gene expression, while all the values >1.0 indicate gene overexpression. The slight increase in expression and production of IL-6, IL-8 and TNF-α is an indicator of physiological inflammation and is justified by the fact that plaque is a group of bacteria which normally colonize the surface of the tooth. The addition of lactoferrin decreases both expression and synthesis of said proinflammatory cytokines, stopping the inflammatory process which might evolve, damaging the cells.

As regards the production of the reactive oxygen species, a reduction in the excretion of superoxides by cells infected with the bacteria contained in the plaque in the presence of lactoferrin has been noticed with respect to the cells infected in the absence of the glycoprotein. In these experiments, iron ions were added to the culture medium at concentrations ranging from 10 to 100 μM, i.e., equal to those which can occur in mucous membranes in pathological situations.

Correlation with In Vivo Tests

Among the three proinflammatory cytokines, it is necessary to stress the importance of IL-6. In patients with gingivitis or other inflammatory forms, an increase in IL-6 in saliva has been determined with respect to the saliva of healthy patients. After one week of treatment with 100 mg of lactoferrin in freeze-dried form, applied to the mucous membranes of the dental arches by brushing twice a day after accurate tooth cleaning, the value of IL-6 decreased and the inflammation and bleeding disappeared.

If the patients did not show altered values of sideremia and hemoglobin, lactoferrin was not administered orally; otherwise, these values returned to normal after one month of treatment with 100 mg of 15-30% saturated lactoferrin twice a day.

EXAMPLE 2

Activity of lactoferrin in parodontopathies. The experimental regimen used consists of the following:

Microorganisms: *Prevotella intermedia* or a sub-gingival plaque, isolated in strict anaerobiosis from a patient affected by parodontopathies, was used at a concentration of $10^7$ bacteria/ml.

Cell monolayer: gingival fibroblasts were cultured until a semiconfluent monolayer of $10^5$ cells/ml was achieved.

Infection of cell monolayer: the gingival fibroblast monolayer was inoculated with $10^7$ bacteria/ml of *Prevotella intermedia* or of anaerobic Gram-negative bacteria of the subgingival plaque in order to have a microbial infection multiplicity of 100:1 in the absence or presence of 60 μg/ml of saturated bovine lactoferrin in iron at 15-30% and incubated for 4 h at 37° C.

Dosage of cytokine expression: the supernatant of the monolayer that was subjected to infection for 4 h was collected and centrifuged in order to remove the bacteria. After repeated centrifugations, the bacteria-free supernatant was frozen at −20° C. for analysis of the production of any cytokines induced by the infection. The monolayer was instead washed repeatedly with PBS without $Ca^{2+}$ and $Mg^{2+}$ in order to remove both the bacteria and any traces of lactoferrin, in the conditions in which it had been added, and lysed in order to extract the RNAs from the fibroblasts and test them, for gene expression, in comparison with those extracted from cells that were not infected or were infected in the absence of lactoferrin, by means of a Microarray.

Dosage of production of expressed cytokines: the preserved supernatant was used to dose the cytokines produced by means of an immune enzymatic test (ELISA) specific for each cytokine to be tested.

Superoxide Assay

The production of the reactive oxygen species was measured by adding ferricytochrome c to the epithelial cells in culture. The assay was based on reduction of ferricytochrome c.

The results of the experiments are summarized hereafter:

Among the 300 genes analyzed, infection of the cell monolayer with *Prevotella intermedia* and with subgingival plaque induced a gene expression which was approximately 3 to 10 times greater than the non-infected one for interleukin 1-α, interleukin 1-β, for interleukin 6, interleukin 8, GRO1, GRO2, GRO3, TNF-α, NF-kB, NF-kBIA.

The addition of lactoferrin reduced the expression of all these cytokines, returning them to normal expression values, except for IL-8, which although reduced considerably still remained overexpressed. Quantitative analysis of the synthesis, reported only for the most important cytokines such as interleukin 1-β, interleukin 6, interleukin 8 and TNF-α, confirms the data related to the gene expression of these proinflammatory cytokines, as reported in Table 2.

TABLE 2

Expression and synthesis of interleukin 1β (IL-1β), interleukin 6 (IL-6), interleukin 8 (IL-8) and of TNF-α in gingival fibroblasts infected or not with *Prevotella intermedia* in the absence or presence of lactofenin (60 μg/ml).

|  | Without lactoferrin | | | | With lactoferrin | | | |
| --- | --- | --- | --- | --- | --- | --- | --- | --- |
|  | IL-1β | IL-6 | IL-8 | TNF-α | IL-1β | IL-6 | IL-8 | TNF-α |
| Expression in non-infected cells | 1.0 | 1.0 | 1.0 | 1.0 | 1.0 | 1.0 | 1.0 | 1.0 |
| Expression in infected cells | 3.0 | 9.1 | 9.5 | 5.4 | 0.7 | 0.4 | 3.5 | 1.0 |
| Synthesis in non-infected cells (pg/ml) | 1.000 | 90 | 2.100 | 22 | 1.000 | 90 | 2.100 | 22 |
| Synthesis in infected cells (pg/ml) | 5.000 | 900 | 10.000 | 120 | 900 | 80 | 5.800 | 18 |

The value 1.0 given in the Table relates to a normal gene expression, while all the values >1.0 indicate gene overexpression. The expression and production of IL-1β, IL-6, IL-8 and TNF-α by fibroblasts infected by *Prevotella intermedia* is greater than those observed in the infection of gingival fibroblasts with plaque bacteria. These data indicate that the capacity to penetrate within the cells of the host is possessed only by anaerobic Gram-negative bacteria, associated with parodontopathies, such as *Prevotella intermedia*, and not by adhesive and non-invasive bacteria that induce gingivitides, causes a much higher inflammatory response, which can be considered destructive, as demonstrated when the bacteria remain in vitro for more than 4 h inside the cells. The addition of lactoferrin reduces considerably not only the expression and synthesis of the IL-6, IL-8, and TNF-α, but also of interleukin 1-α, interleukin 1β, GRO1, GRO2, GRO3, NF-kB and NF-kBIA, confirming its great importance in returning the values of proinflammatory cytokines to normal values, except for IL-8, which might be a signal of the permanence of bacteria inside the host cells. Similar data have been obtained by using as infectious agent the anaerobic Gram-negative bacteria that are present in subgingival plaque.

The production of superoxides by epithelial cells is considerable when the bacteria enter the cell in the absence of lactoferrin, but is inhibited by the presence of lactoferrin.
Correlation with In Vivo Tests In the crevicular fluid of patients with parodontopathy, an increase in the concentration of IL-1β, IL-6 and iron was observed with respect to healthy patients. After a one-month treatment with 100 mg of lactoferrin in freeze-dried form, applied to the mucous membranes of the dental arches by brushing twice a day after accurate teeth cleaning, the value of IL-1β, IL-6 and of iron in the crevicular fluid decreased together with the disappearance of bleeding, of subgingival abscesses, of inflammation, and the attachment of the tooth was restored starting from the third week of the treatment. If the patients did not show altered values of sideremia and hemoglobin, oral administration of lactoferrin was not performed; otherwise, treatment with 100 mg of lactoferrin saturated at 15-30% twice a day for one month was performed. After one month of this oral therapy, these values returned to normal, together with a decrease in the concentration of IL-6 and hepcidin in blood or of hepcidin in urine with respect to before the treatment.

EXAMPLE 3

Activity of lactoferrin in infections due to type 1 Herpesvirus associated with parodontopathies and labial herpes and due to type 2 Herpesvirus associated with genital herpes. The experimental regimen used consisted of the following:
Virus The tests were conducted by using types 1 and 2 Herpesvirus (HSV-1 and HSV-2).
Viral Infection of the Monolayer The cell monolayer (fibroblasts or HeLa) was incubated at 4° C. for 1 h in the absence or in the presence of 500 μg/ml of lactoferrin with HSV-1 or HSV-2. After this period had elapsed, the monolayer was placed at 37° C.
Dosage of Production of Interleukin 6

The supernatant of the cultures was assayed to determine the production of interleukin 6 by means of the specific immune enzyme test (ELISA).
The Results of the Experiments are Summarized Below:

The infection of the monolayers with HSV-1 or HSV-2 induced a higher secretion of interleukin 6 with respect to those non-infected. The addition of lactoferrin reduced considerably the expression and synthesis of the inflammatory cytokines and in particular of interleukin 6, as listed in Table 3.

TABLE 3

Expression and synthesis of interleukin 6 (IL-6) in gingival fibroblasts or in HeLa cells infected or not with type 1 and 2 Herpesvirus.

|  | Without lactoferrin IL-6 | With lactoferrin IL-6 |
| --- | --- | --- |
| Expression in non-infected cells | 1.0 | 1.0 |
| Expression in infected cells | 2.5 | 1.0 |
| Synthesis in non-infected cells (pg/ml) | 90 | 90 |
| Synthesis in cells infected (pg/ml) | 320 | 110 |

The value 1.0 given in the Table refers to a normal gene expression, while all the values >1.0 indicate a gene overexpression. The data obtained with HSV-1 or HSV-2 are similar.
Correlation with In Vivo Tests After the one-month treatment with 100 mg of lactoferrin in freeze-dried form, applied to the dental arches by brushing or on the labial or genital lesion twice a day after accurate hygiene, the value of the proinflammatory cytokines, including IL-6, and of the concentration of iron reduced together, in the case of disorders of the oral cavity, with the disappearance of bleeding, of subgingival abscesses, of the destructive inflammation, which can entail the loss of the attachment of the tooth; whereas in the case of a labial or genital herpes, the lesion and the corresponding inflammation disappeared after 4 or 7 days of treatment. If the patients did not show altered values of sideremia and hemoglobin, oral administration of lactoferrin was not performed. In the case of patients with many relapses, hypoferremia, anemia and high values of IL-6 and hepcidin were observed. In these cases, a treatment with 100 mg of lactoferrin saturated at 15-30% twice a day for 1 month was performed. After one month of the described therapy, said values returned to normal, together with a reduction in the concentration of IL-6 and hepcidin in blood or of hepcidin in urine with respect to before the treatment.

EXAMPLE 4

Activity of lactoferrin in mycoses of the oral cavity. The experimental regimen used consisted of the following:

Microorganisms: a strain of *Candida albicans*, isolated clinically, was used at a concentration equal to $10^7$ cells/ml.

Cell monolayer: gingival fibroblasts were cultured until a semiconfluent monolayer of $10^5$ cells/ml was obtained.

Infection of the cell monolayer: the monolayer of gingival fibroblasts was inoculated with $10^7$ *C. albicans*/ml in order to have an infection multiplicity equal to 100:1 in the absence or in the presence of 60 µg/ml of bovine lactoferrin saturated in iron at 15-30% and incubated for 2 h at 37° C.

Dosage of the expression of cytokines: the supernatant of the monolayer was collected and centrifuged in order to remove the cells of *C. albicans*. After repeated centrifugations, the supernatant without *C. albicans* was frozen at −20° C. for analysis of production of any cytokines induced by the infection. The monolayer was instead washed repeatedly with PBS without $Ca^{2+}$ and $Mg^{2+}$ in order to remove both *C. albicans* and any traces of lactoferrin, in the conditions in which it was added, and lysed in order to extract the RNAs of the fibroblasts in order to test them, for gene expression, in comparison with those extracted from the infected or non-infected cells in the absence of lactoferrin by means of a Microarray.

Dosage of production of expressed cytokines: the preserved supernatant was used to dose the cytokines produced by means of an immune enzymatic test (ELISA) specific for each cytokine to be tested.

Assay of the Superoxides

The production of the reactive oxygen species was measured by means of the addition of ferricytochrome c to the epithelial cells in culture. The assay is based on the reduction of ferricytochrome c.

The results of the experiments are summarized below:

Among the 300 genes analyzed, the infection of the monolayer induced gene expression which with respect to the non-infected cells was approximately 2 times higher only for interleukin 6. The addition of lactoferrin reduced the expression of IL-6, returning it to a normal expression value. Quantitative analysis of the synthesis of interleukin 6 confirmed the data related to the gene expression of said proinflammatory cytokine, as listed in Table 4.

TABLE 4

Expression and synthesis of interleukin 6 (IL-6) in gingival fibroblasts infected or not with *C. albicans* in the absence or in the presence of lactoferrin (60 µg/ml).

|  | Without lactoferrin IL-6 | With lactoferrin IL-6 |
|---|---|---|
| Expression in non-infected cells | 1.0 | 1.0 |
| Expression in infected cells | 2.0 | 1.0 |
| Synthesis in non-infected cells (pg/ml) | 90 | 90 |
| Synthesis in infected cells (pg/ml) | 240 | 130 |

The value 1.0 given in the Table refers to a normal gene expression, while all the values >1.0 indicate gene overexpression. The values of the expression and production of IL-6 are higher than those observed in the infection of gingival fibroblasts with bacteria contained in plaque. The addition of lactoferrin, also in infections due to *Candida albicans*, reduces both expression and synthesis of IL-6.

As regards the production of reactive oxygen species, a reduction of the excretion of superoxides was observed on the part of the cells infected with *Candida albicans* in the presence of lactoferrin with respect to those infected again with *Candida albicans* in the absence of the glycoprotein.

Correlation with In Vivo Tests

In the saliva of patients affected by infection with *Candida albicans*, IL-6 is present in a higher concentration than that observed in the saliva of healthy patients. After one week of treatment with 100 mg of lactoferrin in freeze-dried form, applied to the dental arches by brushing, twice a day after accurate cleaning of the teeth, the value of IL-6 decreased together with the disappearance of the inflammation and of the infection.

If the patients did not show altered values of sideremia and hemoglobin, oral administration of lactoferrin was not performed; otherwise, oral administration of 100 mg of lactoferrin saturated at 15-30% was performed twice a day for 1 month, obtaining restoration of the physiological values of sideremia and hemoglobin.

EXAMPLE 5

Activity of lactoferrin in vaginal mycoses. The experimental regimen used consisted of the following:

Microorganisms: a strain of *Candida albicans*, isolated from a patient affected by vaginitis, was used at a concentration of $10^7$ cells/ml.

Cell monolayer: HeLa cells derived from uterine carcinoma were cultured until a semiconfluent monolayer of $10^5$ cells/ml was obtained.

Infection of the cell monolayer: the monolayer of gingival fibroblasts was inoculated with $10^7$ *C. albicans*/m in order to have an infection multiplicity of 100:1 in the absence or in the presence of 60 µg/ml of bovine lactoferrin saturated in iron at 15-30% and incubated for 2 h at 37° C.

Dosage of cytokine expression: the supernatant of the monolayer was collected and centrifuged in order to remove the cells of *C. albicans*. After repeated centrifugations, the supernatant without *C. albicans* was frozen at −20° C. for analysis of production of any cytokines induced by the infection. The monolayer was instead washed repeatedly with PBS without $Ca^{2+}$ and $Mg^{2+}$ in order to remove both *C. albicans* and any traces of lactoferrin, in the conditions in which it was added, and lysed in order to extract the RNAs from the HeLa cells in order to test them, for gene expression, in comparison with those extracted from the infected cells in the absence of lactoferrin, by means of a Microarray.

Dosage of production of expressed cytokines: the preserved supernatant was used to dose the produced cytokines by means of an immune enzymatic test (ELISA) specific for each cytokine to be tested.

Assay of the Superoxides

The production of the reactive oxygen species was measured by means of the addition of ferricytochrome c to the epithelial cells in culture. The assay was based on the reduction of ferricytochrome c.

The results of the experiments are summarized below:

Among the 300 genes analyzed, the infection of the monolayer induced a gene expression which compared to the non-infected cells was approximately 2 times higher only for interleukin 6. The addition of lactoferrin reduced the expression of IL-6, returning it to a normal expression value. Quantitative analysis of the synthesis of interleukin 6 confirmed the data related to gene expression of said proinflammatory cytokine, as listed in Table 5.

TABLE 5

Expression and synthesis of interleukin 6 (IL-6) by HeLa cells infected or not with *C. albicans* in the absence or in the presence of lactoferrin (500 µg/ml).

|  | Without lactoferrin IL-6 | With lactoferrin IL-6 |
|---|---|---|
| Expression in non-infected cells | 1.0 | 1.0 |
| Expression in infected cells | 2.0 | 1.0 |
| Synthesis in non-infected cells (pg/ml) | 90 | 90 |
| Synthesis in infected cells (pg/ml) | 200 | 95 |

The value 1.0 given in the Table relates to normal gene expression, while all the values >1.0 indicate gene overexpression. The addition of lactoferrin, in cells infected by *Candida albicans*, reduces both expression and synthesis of IL-6.

As regards the production of reactive oxygen species, a reduction of the excretion of superoxides by the cells infected by *Candida albicans* in the presence of lactoferrin was observed with respect to those infected, again with *Candida albicans*, in the absence of the protein.

Correlation with the In Vivo Tests

In the vaginal secretions of patients affected by vaginal infections supported by *Candida albicans*, IL-6 is present in a higher concentration than that observed in healthy patients. After a one-week treatment with 100 mg of lactoferrin in freeze-dried form, applied in vagina twice a day after accurate hygiene, the value of IL-6 in vaginal secretion decreased, and the inflammation and infection disappeared. If the patients did not show altered values of sideremia and hemoglobin, oral administration of lactoferrin was not performed; otherwise, oral administration of 100 mg of lactoferrin saturated at 15-30% was performed twice a day for 1 month, obtaining restoration of the physiological values of sideremia and hemoglobin.

EXAMPLE 6

Activity of lactoferrin in enteritides. The experimental regimen used consisted of the following:

Microorganisms: a strain of *Salmonella typhi*, isolated clinically, was used at a concentration of $10^7$ cells/ml.

Cell monolayer: intestinal cells, CaCo-2, were cultured until a semiconfluent monolayer of $10^5$ cells/ml was obtained.

Infection of the cell monolayer: the monolayer of intestinal cells was inoculated with $10^7$ *S. typhi*/ml in order to have an infection multiplicity of 100:1 in the absence or in the presence of 60 µg/ml of bovine lactoferrin saturated in iron at 15-30% and incubated for 2 h at 37° C.

Dosage of cytokine expression: the supernatant of the monolayer was collected and centrifuged in order to remove the cells of *S. typhi*. After repeated centrifugations, the supernatant without *S. typhi* was frozen at −20° C. for analysis of production of any cytokines induced by the infection. The monolayer was instead washed repeatedly with PBS without $Ca^{2+}$ and $Mg^{2+}$ in order to remove both *S. typhi* and any traces of lactoferrin, in the conditions in which it was added, and lysed in order to extract the RNAs from the CaCo-2 cells in order to test them, for gene expression, in comparison with those extracted from infected cells in the absence of lactoferrin by means of a Microarray.

Dosage of production of the expressed cytokines: the preserved supernatant was used to dose the cytokines produced by means of an immune enzymatic test (ELISA) specific for each cytokine to be tested.

Assay of the Superoxides

The production of the reactive oxygen species was measured by adding ferricytochrome c to the cultured epithelial cells. The assay is based on the reduction of ferricytochrome c.

The results of the experiments are summarized below:

Among the 300 analyzed genes, the infection of the monolayer induced gene expression, which compared to the non-infected cells, was approximately 2 times higher only for interleukin 6. The addition of lactoferrin reduced the expression of IL-6, returning it to a normal expression value. Quantitative analysis of the synthesis of interleukin 6 confirmed the data related to gene expression of this proinflammatory cytokine, as listed in Table 6.

TABLE 6

Expression and synthesis of interleukin 1β, interleukin 6 (IL-6), interleukin 8 (IL-8) and TNF-α in intestinal cells infected or not with *Salmonella typhi* in the absence or in the presence of lactoferrin (60 µg/ml).

|  | Without lactoferrin | | | | With lactoferrin | | | |
|---|---|---|---|---|---|---|---|---|
|  | IL-1β | IL-6 | IL-8 | TNF-α | IL-1β | IL-6 | IL-8 | TNF-α |
| Expression in non-infected cells | 1.0 | 1.0 | 1.0 | 1.0 | 1.0 | 1.0 | 1.0 | 1.0 |
| Expression in infected cells | 3.0 | 8.1 | 9.2 | 5.0 | 0.9 | 0.5 | 3.0 | 1.0 |

TABLE 6-continued

Expression and synthesis of interleukin 1β, interleukin 6 (IL-6),
interleukin 8 (IL-8) and TNF-α in intestinal cells infected or not with
*Salmonella typhi* in the absence or in the presence of lactoferrin (60 µg/ml).

|  | Without lactoferrin | | | | With lactoferrin | | | |
| --- | --- | --- | --- | --- | --- | --- | --- | --- |
|  | IL-1β | IL-6 | IL-8 | TNF-α | IL-1β | IL-6 | IL-8 | TNF-α |
| Synthesis in non-infected cells (pg/ml) | 1.000 | 90 | 2.100 | 22 | 1.000 | 90 | 2.100 | 22 |
| Synthesis in infected cells (pg/ml) | 4.500 | 850 | 9.000 | 120 | 800 | 80 | 3.800 | 15 |

EXAMPLE 7

Capsules for oral administration in the treatment of hypoferremia and anemia.

Whatever the cause of states of hypoferremia and anemia, the administration for one month of a capsule containing 100 mg of lactoferrin twice a day restored the normal values of sideremia and hemoglobin. The resulting quantitative data are summarized in Table 7 and can be attributed to all the in vivo treatments, to which examples 1, 2, 3, 4, 5 and 6 refer.

TABLE 7

Average values of hemoglobin and sideremia of 150 patients,
before and after treatment with 100 mg of lactoferrin 2 times per day.

| Before the treatment | | After treatment with lactoferrin 100 mg 2 per day | |
| --- | --- | --- | --- |
| Hemoglobin g/dl Range and average values | Sideremia µg/ml Range and average values | Hemoglobin g/dl Range and average values | Sideremia µg/ml Range and average values |
| 10.1-11.9 11.0 | 25-64 44.5 | 12.2-13.5 12.8 | 80-130 105.0 |

Moreover, the values of hepcidin and of IL-6 assayed after an administration of lactoferrin for one month were lower than those before therapy. In particular, hepcidin decreased from 160 ng/ml to 100 ng/ml in blood, and from 1000 ng/mg of creatinine per day to 10 ng/mg of creatinine per day in urine. As regards IL-6, after one month of treatment with lactoferrin, its concentration in blood decreased from 7.5 in men and 5.4 pg/ml in women to approximately 2.4 and to 1.2 pg/ml, respectively.

EXAMPLE 8

Freeze-dried product for oral use. Use: deposition of 100 mg of lactoferrin on the mucous membranes of the oral cavity twice a day after accurate oral hygiene.

| Active ingredient: | 100 mg of freeze-dried lactoferrin | |
| --- | --- | --- |
| Excipients: | sodium bicarbonate | 25 mg |
|  | sodium citrate | 25 mg |

EXAMPLE 9

Freeze-dried product for vaginal use. Use: deposition of 100 mg of lactoferrin on vaginal mucous membranes twice a day after accurate hygiene.
Active ingredient: 100 mg of freeze-dried lactoferrin

EXAMPLE 10

Solution for oral use. Use: a rinse of approximately 10-15 ml twice a day after accurate oral hygiene.
Composition for 100 ml:
Active ingredient: solution in water or in solvents usually used for oral solutions containing 1% lactoferrin to be dissolved at the time of use.

EXAMPLE 11

Solution for vaginal use. Use: a wash of approximately 20-25 ml twice a day after accurate hygiene.
Composition for 100 ml:
Active ingredient: solution in water or in solvents usually used for vaginal solutions containing 1% lactoferrin to be dissolved at the time of use.

EXAMPLE 12

Gel or cream for oral use. Use: application twice a day after accurate oral hygiene.
Composition for 100 g
Active ingredient: lactoferrin is incorporated at 1% concentration in the cream or gel,
Excipients: common to all gels or creams for applications on mucous membranes.

EXAMPLE 13

Gel or cream for vaginal use. Use: application twice a day after accurate hygiene.
Composition for 100 g:
Active ingredient: lactoferrin is incorporated at 1% concentration in the cream or gel,
Excipients: common to all gels or creams for applications on the vaginal mucosa.

EXAMPLE 14

Tablets for topical use. Use: one tablet to be dissolved in the mouth twice a day after accurate oral hygiene.

| Composition for 300 mg: | | |
| --- | --- | --- |
| Active ingredient: | 100 mg of lactoferrin | |
| Excipients: | sodium benzoate | 150 mg |
|  | Peppermint oil | 50 mg |

EXAMPLE 15

Vaginal tablets. Use: one tablet to be applied in vagina twice a day after accurate hygiene.

Composition for 300 mg:
Active ingredient: 100 mg of lactoferrin
Excipients: sodium benzoate 150 mg
sodium bicarbonate 50 mg

EXAMPLE 16

Toothpaste. Use: at least twice a day.
Composition for 100 mg
Active ingredient: lactoferrin 500 mg
Excipients: common to all toothpastes, plus 50 mg sodium bicarbonate and 50 mg sodium citrate.

EXAMPLE 17

Chewing gum. Use: 1 chewing gum to be chewed after each meal.

| Active ingredient: | lactoferrin | 500 mg |
|---|---|---|
| Excipients: | base gum | 400 mg |
| | sodium citrate | 10 mg |
| | sodium bicarbonate | 10 mg |
| | hydroxybenzoate | 20 mg |
| | essences | 5 mg |

EXAMPLE 18

Freeze-dried product to be dissolved in water and frozen. Use: massage of the gums two or more times per day
Composition for 10 ml:
Active ingredient: 20 mg of lactoferrin
Excipients: essences 5 mg

EXAMPLE 19

Capsules to be swallowed. Use: 1 capsule twice a day away from meals.
Composition Per Capsule:
Active ingredient: 100 mg of lactoferrin
Excipients: sodium bicarbonate 25 mg The examples given above demonstrate the capacity of lactoferrin to inhibit the expression and synthesis of proinflammatory cytokines by gingival fibroblasts infected by bacteria contained in a plaque, taken from a patient, together with the activity of protecting the cells against the damage caused by superoxides, according to an experimental model which is described, repeatable and reproducible. The examples given above also demonstrate the capacity of lactoferrin to inhibit the expression and synthesis of proinflammatory cytokines by gingival fibroblasts infected by *Prevotella intermedia* or by anaerobic Gram-negative bacteria present in the subgingival plaque, together with the activity of protecting the cells against damage caused by superoxides, according to an experimental model which is described, repeatable and reproducible. The examples given above also demonstrate the capacity of lactoferrin to inhibit the expression and synthesis of proinflammatory cytokines by gingival fibroblasts or by HeLa cells infected by *Candida albicans*, together with the activity of protecting the cells against damage caused by superoxides, according to an experimental model which is described, repeatable and reproducible. The examples given above also demonstrate the capacity of lactoferrin to inhibit the expression and synthesis of proinflammatory cytokines on the part of intestinal cells infected by *Salmonella* spp, together with the activity of protecting the cells against damage caused by superoxides, according to an experimental model which is described, repeatable and reproducible. In the in vivo tests, in all the cases in which hypoferremia and anemia were found at the infection and inflammation of the mucous membranes, before and after oral administration of lactoferrin for at least one month, analysis of IL-6 and of hepcidin in blood or in urine was performed together with analysis of the hematological values, so as to demonstrate the effectiveness of the invention in restoring the homeostasis of the iron in circulation and deposited in tissues. Therefore, it has been fully demonstrated that the use of at least one transferrin, preferably lactoferrin, for the preparation of a medicament for topical and/or oral administration achieves the aim and objects mentioned above.

Although only some preferred embodiments of the invention have been described in the text, the person skilled in the art will understand immediately that it is in any case possible to obtain other equally advantageous and preferred embodiments.

The disclosures in Italian Patent Application no. MI2005A002351, from which this application claims priority, are incorporated herein by reference.

What is claimed is:

1. A method for treating destructive inflammation of a mucous membrane in a patient in need thereof, said method consisting of:
    topically administering to a patient a topical pharmaceutical composition comprising purified bovine lactoferrin, wherein the patient has destructive inflammation of a mucous membrane caused by an infection selected from the group consisting of a gingivitis, a viral gingivostomatitis, a Gram-negative anaerobic bacterial parodontopathy, a Herpes simplex virus (HSV) 1 infection, an HSV 2 infection, and a *Candida albicans* infection,
    wherein a total of 100 mg to 400 mg purified bovine lactoferrin is topically applied daily to the inflamed mucous membrane of the patient.

2. The method according to claim 1, wherein the infection is selected from the group consisting of a gingivitis, a viral gingivostomatitis, and a Gram-negative anaerobic bacterial parodontopathy.

3. The method according to claim 1, wherein the inflamed mucous membrane is selected from the group consisting of a vaginal mucous membrane, an anal mucous membrane, and an oropharyngeal cavity mucous membrane.

4. The method of claim 1 wherein the purified bovine lactoferrin has any degree of saturation with one or more of iron(III), zinc, copper, or manganese.

5. The method according to claim 1 wherein the purified bovine lactoferrin is recombinant bovine lactoferrin.

6. The method of claim 1 wherein the purified bovine lactoferrin is a polypeptide fragment, and wherein the polypeptide fragment is either lobe N or lobe C of the bovine lactoferrin.

7. The method of claim 1, wherein destructive inflammation is characterized by overproduction in the patient of interleukin-6 and hepcidin.

8. The method of claim 1, wherein a total of 100 mg to 400 mg purified bovine lactoferrin is topically applied daily to the mucous membrane of the patient for at least one week.

9. The method of claim 1, wherein 50 mg to 200 mg purified bovine lactoferrin is topically applied twice daily to the mucous membrane of the patient.

10. The method of claim 7, wherein the topical pharmaceutical composition is a powder comprising 50 mg to 200 mg freeze dried bovine lactoferrin.

11. A method for treating destructive inflammation of a mucous membrane in a patient in need thereof, wherein the patient has hypoferremia or anemia caused by the destructive inflammation, said method consisting of:

topically administering to a patient a topical pharmaceutical composition comprising purified bovine lactoferrin, wherein the patient has destructive inflammation of a mucous membrane caused by an infection selected from the group consisting of a gingivitis, a viral gingivostomatitis, a Gram-negative anaerobic bacterial parodontopathy, a Herpes simplex virus (HSV) 1 infection, an HSV 2 infection, and a *Candida albicans* infection, wherein a total of 100 mg to 400 mg purified bovine lactoferrin is topically applied daily to the inflamed mucous membrane of the patient; and orally administering a second pharmaceutical composition comprising purified bovine lactoferrin, to the patient to treat the hypoferremia or anemia, wherein the second pharmaceutical composition is formulated as a capsule or a tablet for oral ingestion and wherein a total of 50 mg to 200 mg purified bovine lactoferrin is administered daily to the patient in the form of the second pharmaceutical composition.

12. The method according to claim 11, wherein treating the hypoferremia or anemia comprises restoring a physiological distribution of the quantity of iron between tissues and circulation.

13. The method of claim 11, wherein the topical pharmaceutical composition and the second pharmaceutical composition formulated for oral ingestion are administered simultaneously or sequentially.

14. The method of claim 11, wherein the daily oral administration is for at least one month.

15. The method of claim 11, wherein the daily oral administration is 200 mg purified bovine lactoferrin.

16. The method of claim 11, wherein 50 mg to 100 mg purified bovine lactoferrin is orally administered twice daily to the patient.

17. The method according to claim 11, wherein the inflamed mucous membrane is a vaginal mucous membrane, an anal mucous membrane, and or oropharyngeal cavity mucous membrane.

18. The method according to claim 11 wherein the purified bovine lactoferrin is recombinant bovine lactoferrin.

19. The method of claim 11 wherein the purified bovine lactoferrin is a polypeptide fragment, and wherein the polypeptide fragment is either lobe N or lobe C of the bovine lactoferrin.

* * * * *